United States Patent
Stochniol et al.

(10) Patent No.: US 10,196,327 B2
(45) Date of Patent: Feb. 5, 2019

(54) PRODUCTION OF AT LEAST 1-HEXENE AND OCTENE FROM ETHENE

(71) Applicant: Evonik Degussa GmbH, Essen (DE)

(72) Inventors: Guido Stochniol, Haltern am See (DE); Helene Reeker, Dortmund (DE); Dietrich Maschmeyer, Recklinghausen (DE); Stephan Peitz, Oer-Erkenschwick (DE); Jörg Schallenberg, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 21 days.

(21) Appl. No.: 15/623,631

(22) Filed: Jun. 15, 2017

(65) Prior Publication Data

US 2018/0009726 A1  Jan. 11, 2018

(30) Foreign Application Priority Data

Jul. 8, 2016 (EP) ..................................... 16178531

(51) Int. Cl.
*B01D 3/14* (2006.01)
*C07C 1/20* (2006.01)
(Continued)

(52) U.S. Cl.
CPC .................. *C07C 2/04* (2013.01); *B01D 3/14* (2013.01); *B01J 19/18* (2013.01); *C01B 33/12* (2013.01);
(Continued)

(58) Field of Classification Search
CPC combination set(s) only.
See application file for complete search history.

(56) References Cited

U.S. PATENT DOCUMENTS 2,581,228 A  1/1952  Bailey et al.
4,751,343 A * 6/1988  Reinhardt ................. C07C 1/20
                                                      585/639
(Continued)

FOREIGN PATENT DOCUMENTS

WO    9511874 A1   5/1995
WO    2004052809 A1   6/2004
WO    2015083053 A1   6/2015

OTHER PUBLICATIONS

European Search Report dated Jan. 2, 2017 in EP 16178531.6 (7 pages).
Reeker et al., U.S. Appl. No. 15/605,170, filed May 25, 2017.

*Primary Examiner* — In Suk C Bullock
*Assistant Examiner* — Ali Z Fadhel
(74) *Attorney, Agent, or Firm* — Philip P. McCann; Nexsen Pruet, PLLC (57) ABSTRACT

The invention is concerned with the production of 1-hexene and octenes from ethene. 1-Butene is optionally also to be produced. The problem addressed by the present invention is that of developing a process for producing 1-hexene from ethene by MTHxE etherification to achieve better chemical utilization of the employed carbon atoms. This problem is solved by catalytic retrocleavage of MTHxE into the $C_6$ olefins and the alcohol, reuse of the alcohol in the etherification and reaction of the obtained $C_6$ olefins with ethene to afford $C_8$ olefins. In this way the alcohol is not lost from the process but rather is internally recirculated as a derivatizing agent. The less attractive $C_6$ olefins from the cleavage product are upgraded to octene with further ethene in order to provide a further commercial product.

20 Claims, 6 Drawing Sheets

(51) Int. Cl.
| | |
|---|---|
| C07C 2/04 | (2006.01) |
| C07C 2/10 | (2006.01) |
| C07C 2/24 | (2006.01) |
| C07C 2/26 | (2006.01) |
| B01J 19/18 | (2006.01) |
| C01B 33/12 | (2006.01) |
| C01F 11/02 | (2006.01) |
| C07C 11/02 | (2006.01) |
| C07C 11/08 | (2006.01) |
| C07C 41/06 | (2006.01) |
| C07C 43/04 | (2006.01) |
| C07C 11/107 | (2006.01) |
| C07C 11/113 | (2006.01) |

(52) U.S. Cl.
CPC ............ *C01F 11/02* (2013.01); *C07C 1/20* (2013.01); *C07C 2/10* (2013.01); *C07C 2/24* (2013.01); *C07C 2/26* (2013.01); *C07C 41/06* (2013.01); *C07C 2521/06* (2013.01); *C07C 2521/08* (2013.01); *C07C 2521/10* (2013.01); *C07C 2523/26* (2013.01); *C07C 2523/745* (2013.01); *C07C 2523/755* (2013.01); *C07C 2531/12* (2013.01); *Y02P 20/52* (2015.11); *Y02P 30/42* (2015.11)

(56) References Cited

U.S. PATENT DOCUMENTS

| | | | |
|---|---|---|---|
| 5,095,164 A * | 3/1992 | Gabel | B01D 3/009 568/66 |
| 5,463,157 A * | 10/1995 | Hendriksen | C07C 1/20 562/521 |
| 5,752,992 A | 5/1998 | Hendriksen | |
| 7,294,741 B2 | 11/2007 | Bub et al. | |
| 7,342,144 B2 | 3/2008 | Kaizik et al. | |
| 7,939,597 B2 | 5/2011 | Bub et al. | |
| 8,198,481 B2 | 6/2012 | Kuppinger et al. | |
| 8,258,249 B2 | 9/2012 | Bub et al. | |
| 8,293,941 B2 | 10/2012 | Kuppinger et al. | |
| 8,481,784 B2 | 7/2013 | Kuppinger et al. | |
| 8,524,945 B2 | 9/2013 | Stochniol et al. | |
| 8,895,683 B2 | 11/2014 | Kuppinger et al. | |
| 2006/0276334 A1 | 12/2006 | Balduf et al. | |
| 2008/0058573 A1* | 3/2008 | Zanthoff | B01J 19/30 585/649 |
| 2009/0068440 A1 | 3/2009 | Bub et al. | |
| 2010/0099934 A1* | 4/2010 | Gartside | C07C 11/107 585/314 |
| 2016/0207848 A1 | 7/2016 | Stochniol et al. | |
| 2016/0207849 A1 | 7/2016 | Stochniol et al. | |
| 2016/0257630 A1 | 9/2016 | Stochniol et al. | |
| 2017/0355651 A1 | 12/2017 | Reeker et al. | |

\* cited by examiner

PRODUCTION OF AT LEAST 1-HEXENE AND OCTENE FROM ETHENE

This application claims the benefit of European Application No. 16178531.6 filed on Jul. 8, 2016, the disclosure of which is expressly incorporated herein by reference.

The invention is concerned with the production of 1-hexene and octenes from ethene. 1-Butene is optionally also to be produced.

BACKGROUND

Hydrocarbons are chemical compounds which consist exclusively of carbon and hydrogen. Alkenes (synonym: olefins) are hydrocarbons which have a C=C double bond in the molecule. Alkanes (synonym: paraffins), on the other hand, are hydrocarbons which have only single bonds. They are therefore also referred to as saturated.

In organic chemistry, hydrocarbons are frequently designated according to the number of carbon atoms which they have per molecule, in that the respective class of substances is preceded by the prefix $C_n$. "n" is the respective number of carbon atoms in a molecule. Thus, $C_4$ olefins are substances from the class of alkenes having four carbon atoms. $C_8$ olefins correspondingly have eight carbon atoms per molecule. Where the prefix $C_{n+}$ is used hereinafter, it refers to a class of substances which have more than n carbon atoms per molecule. A $C_{4+}$ olefin accordingly has at least five carbon atoms.

The simplest olefin is ethene (ethylene). It has two carbon atoms. Ethene is an important commodity chemical and is therefore produced in large quantities. This is usually effected by cracking of naphtha. In addition, it can be obtained by dehydrogenation of ethane, which in turn is a constituent of natural gas. Owing to the increasing exploitation of unconventional sources of natural gas and decreasing recovery of petroleum, the proportion of ethene based on natural gas is steadily increasing. The physical properties of ethene and the production thereof are described in:

Zimmermann, Heinz and Walzl, Roland: Ethylene. Ullmann's Encyclopedia of Industrial Chemistry (2009).

Oligomerization is understood to mean the reaction of hydrocarbons with themselves to form correspondingly longer-chain hydrocarbons, the so-called oligomers. Olefins having from two to eight carbon atoms can be oligomerized quite efficiently.

Thus, for example, olefins having six carbon atoms (hexene) can be formed by oligomerization of two olefins having three carbon atoms. The oligomerization of two molecules with one another is also referred to as dimerization. If, in contrast, three olefins having three carbon atoms are joined to one another (trimerization), the result is an olefin having nine carbon atoms. The tetramerization of ethene results in octenes, i.e. olefins having eight carbon atoms It should be noted that oligomerization always results in a mixture of different oligomers (oligomerizate). Thus the oligomerization of ethane forms not only ethene dimers but also, in parallel, trimers and tetramers. The oligomerizate thus comprises a range of $C_{2+}$ olefins of different lengths.

The oligomers of one carbon atom count are moreover present in different isomeric structures: thus the dimerization of ethene forms the three isomeric $C_4$ olefins 1-butene, cis-2-butene and trans-2-butene, while the trimerization of ethene can form up to ten different $C_6$ olefin isomers, namely 1-hexene, (E)-2-hexene, (Z)-2-hexene, (E)-3-hexene, (Z)-3-hexene, (R)-3-methyl-1-pentene, (S)-3-methyl-1-pentene, (E)-3-methyl-2-pentene, (Z)-3-methyl-2-pentene and 2-ethyl-1-butene. The variety of $C_8$ olefins formed by $C_2$ tetramerization is even greater.

It can therefore be stated that oligomerization of ethene forms a highly complex mixture of different olefins.

However, only the substances 1-butene and 1-hexene, which are used as monomers or comonomers in the production of plastics, are of industrial interest. Olefins having eight carbon atoms may be converted by hydroformylation and hydrogenation into $C_9$ alcohols which in turn serve as starting materials for the production of a very wide variety of PVC plasticizers.

Those oligomerizing ethene are thus faced with the problem of removing the less sought-after substances from the oligomerizate.

Provided that olefins having different numbers of carbon atoms are to be separated this is readily possible by thermal separation methods (distillation) since the different chain lengths result in widely spaced boiling points. However, there is no such hard separation criterion for mixtures of isomers having identical carbon atom counts because the boiling points of the isomers are usually very close together. Distillative separation is then possible only with great apparatus complexity and high energy energy use, thus resulting in a separation that is far too costly.

Thus for example the boiling point of 1-hexene is 63° C. and that of isohexene (correct name: 4-methyl-1-pentene) is 54° C. This small difference in the boiling point makes it uneconomic to obtain the two pure substances 1-hexene and isohexene from a mixture by distillation; even more so when it is not a binary mixture of these two substances that is concerned but rather an oligomerizate having a multiplicity of further $C_6$ olefin isomers whose respective boiling points are likewise within this narrow temperature window.

US2010/0099934A1 employs a trick to economically separate a mixture comprising isohexene and 1-hexene: the $C_6$ olefin mixture is subjected to an etherification step where the isohexene is reacted with methanol to afford ether.

The etherification converts markedly more isohexene than 1-hexene. This affords a reaction mixture which comprises not only 1-hexene but also the ether 3-methyl-3-methoxypentane in place of the isohexene. Since 3-methyl-3-methoxypentane—also known as methyl tert-hexyl ether (MTHxE)—has a higher boiling point than 1-hexene, the 1-hexene can be removed from the MTHxE by distillation at low cost and complexity. In this way, selective isohexene etherification makes it possible to obtain pure 1-hexene from $C_6$ olefin mixtures such as are generated in ethene oligomerization.

With regard to the process described in US2010/0099934A1, the question of what happens to the removed MTHxE remains. An obvious option is to feed the ether mixture into the fuel pool as an anti-knock agent, similarly to the teaching in U.S. Pat. No. 5,752,992. The carbon atoms bound therein are thus ultimately burned and are no longer available as a starting material for high-value specialty chemicals.

It should moreover be noted that ethene oligomerization does not provide any isohexene (4-methyl-1-pentene) at all but rather only the ten $C_6$ olefins listed above. The technical problem of separating 1-hexene and isohexene solved in US2010/0099934A1 consequently does not arise at all in the workup of ethene oligomerizates; on the contrary it must be solved when $C_6$ olefin mixtures originating from metathesis of $C_4$ olefins are to be utilized.

SUMMARY

In the light of this prior art the problem addressed by the present invention is that of developing the known process for producing 1-hexene from ethene to achieve better chemical utilization of the employed carbon atoms.

This problem is solved by catalytic retrocleavage of MTHxE into the $C_6$ olefins and the alcohol, reuse of the alcohol in the etherification and reaction of the obtained $C_6$ olefins with ethene to afford $C_8$ olefins. In this way the alcohol is not lost from the process but rather is internally recirculated as a derivatizing agent. The less attractive $C_6$ olefins from the cleavage product are upgraded to octene with further ethene in order to provide a further commercial product.

DETAILED DESCRIPTION

Specifically, the invention provides a process for producing at least 1-hexene and octene from ethene comprising the steps of:
a) providing a feedstock mixture comprising ethene;
b) subjecting the ethene to a first oligomerization to obtain a first oligomerizate which comprises olefins having less than six carbon atoms, at least the $C_6$ olefins 1-hexene, 3-methyl-cis-2-pentene, 3-methyl-trans-2-pentene and olefins having more than six carbon atoms;
c) distillative workup of the first oligomerizate to obtain a $C_6$ fraction which comprises at least 1-hexene, 3-methyl-cis-2-pentene, 3-methyl-trans-2-pentene,
d) subjecting the $C_6$ fraction to an etherification by addition of an alcohol in the presence of a heterogeneous catalyst to obtain a first reaction mixture comprising at least 1-hexene and 3-methyl-3-methoxypentane;
e) distillative workup of the first reaction mixture to obtain a first target fraction comprising 1-hexene and an ether fraction at least comprising 3-methyl-3-methoxypentane;
f) wherein the ether fraction is subjected to a cleavage reaction to obtain a cleavage product which comprises 3-methyl-cis-2-pentene, 3-methyl-trans-2-pentene and the alcohol;
g) wherein the alcohol is removed from the cleavage product by distillation and reused in the etherification;
h) wherein a first intermediate at least comprising 3-methyl-cis-2-pentene, 3-methyl-trans-2-pentene is removed from the cleavage product by distillation;
i) wherein the first intermediate is reacted with ethene to obtain a second reaction mixture which comprises olefins having at least eight carbon atoms;
k) and wherein a second target fraction comprising octene is obtained from the second reaction mixture by distillation.

The improvement consists in the features f) to k).

The invention is based on the finding that the etherification is reversible and that octenes can be produced from reaction of $C_6$ olefins with ethene. Skilful integration of these process steps into the distillation setup allows the products of value to be obtained with little additional cost and complexity; more on this later.

In a particularly preferred development of the process described here the ethene is used to produce not only 1-hexene and octen but also 1-butene as a third target product. This is achieved as follows:
a) the first oligomerization is performed such that the first oligomerizate comprises 1-butene, cis-2-butene and trans-2-butene;
b) distillative workup of the first oligomerizate affords a $C_4$ fraction which comprises 1-butene, cis-2-butene and trans-2-butene;
c) the $C_4$ fraction is separated by distillation into a third target fraction comprising 1-butene and into a second intermediate which comprises cis-2-butene and trans-2-butene;
d) the second intermediate is subjected to a second oligomerization to obtain a second oligomerizate which comprises olefins having at least eight carbon atoms;
e) the second oligomerizate is worked up by distillation together with the second reaction mixture to obtain the second target fraction.

Provided that the oligomerization of ethene generates the butenes listed in step a) (which will generally be the case) this extension makes it possible to obtain the sought-after 1-butene as a third target product. Less useful 2-butene is converted via the second oligomerization into the $C_8$ fraction and subjected to the workup that exists in any case.

The oligomerization of the ethene will also generate olefins having more than six carbon atoms. These may be worked up together with the corresponding olefins from the second reaction mixture in order to save apparatus costs. A development of the process accordingly provides that the distillative workup of the first oligomerizate affords a $C_{6+}$ fraction which comprises olefins having more than six carbon atoms and that the $C_{6+}$ fraction is worked up by distillation together with the second reaction mixture to obtain the second target fraction.

Provided that 1-butene is also produced from ethene the oligomerization of the 2-butene likewise forms olefins having a chain length of $C_{6+}$ which may be cost-effectively worked up together. A corresponding development of the process accordingly provides that the distillative workup of the first oligomerizate affords a $C_{6+}$ fraction which comprises olefins having more than six carbon atoms and that the $C_{6+}$ fraction is worked up by distillation together with the second reaction mixture and with the second oligomerizate to obtain the second target fraction.

The oligomerization of the ethene may take place in the liquid phase or in the gas phase. Provided that gas phase oligomerization of the ethene is performed the feedstock mixture should comprise more than 95 wt % of ethene and the reaction conditions of the first oligomerization should be chosen such that the first oligomerization is effected in the gas phase. A solid-state catalyst is then required (heterogeneous catalyst).

It is better to perform the first oligomerization in the liquid phase in the presence of a solid-state catalyst because this results in a greater process intensity of the reaction. There are various options for oligomerizing ethene in the liquid state:

A first option consists of dissolving the ethene in a solvent. Accordingly a feedstock mixture which comprises less than 25 wt % of ethene and more than 75 wt % of the solvent is employed. The reaction conditions of the first oligomerization and the concentration of the ethene in the solvent should then be chosen such that the first oligomerization is effected in the liquid phase and the ethene is fully dissolved in the liquid solvent. The ratio of ethene to solvent is then adjusted to a value between 0.1 and 0.5; the temperature is between 20° C. and 150° C. and the pressure is between $1*10^5$ Pa and $50*10^5$ Pa. The catalyst may then either be homogeneously codissolved in the solvent or preferably be present as a heterogeneous catalyst in the form of a solid.

Suitable solvents are in principle substances which exhibit inert behavior in the oligomerization, i.e. essentially do not take part in the reaction. Specifically, $C_3$- to $C_7$-alkanes and $C_3$- to $C_7$-cycloalkanes are suitable solvents (pure or in admixture). Since the solvent exhibits inert behavior it ends up in the first reaction mixture. It is removed from the first oligomerizate by distillation and recycled. In this way the solvent is always recirculated and is therefore not lost. The location of removal of the solvent from the first oligomerizate depends on the boiling point of the solvent. If for example propane or isobutene is employed as solvent these boil before the dimers of ethene and are removed beforehand. If by contrast n-hexane oder n-heptane are used as solvent the removal of the solvent is effected downstream of the hexene removal.

If ethene is present as the only reactive component in the feedstock mixture, depending on the chosen reaction regime, incomplete conversion of ethene may result. Ethene present in excess, and therefore unconverted in the first oligomerization, is removed by distillation from the first oligomerizate and recycled into the first oligomerization.

A particular embodiment of the process provides that the feedstock mixture comprises not only ethene but also olefins having four carbon atoms, wherein the reaction conditions of the first oligomerization and the composition of the feedstock mixture are chosen such that the first oligomerization is effected in the liquid phase and the ethene is fully dissolved in the olefins having four carbon atoms. The idea behind this is to use a reactive material as solvent, namely olefins having four carbon atoms, more particularly 1-butene, cis-2-butene and trans-2-butene. This is because these olefins can be liquefied at comparatively low pressures and are therefore suitable as solvents for ethene. Since the $C_4$ olefins are themselves reactive they are reacted to afford $C_8$ and $C_{8+}$ in the first oligomerization. Since the octenes are in any case obtained as a target fraction and discharged a recirculation of the solvent becomes unnecessary. Admittedly, fresh $C_4$ alkene must always be supplied to the first oligomerization. Since butene-containing mixtures are traded as standard feedstocks in downstream petrochemistry this is in most cases not a problem.

However, if no $C_4$ source is available, $C_6$ olefin, which is in any case formed in the process by ethene trimerization, may be used as reactive solvent. A preferred variant of the process therefore provides that the feedstock mixture comprises not only ethene but also olefins having six carbon atoms, wherein the reaction conditions of the first oligomerization and the composition of the feedstock mixture are chosen such that the first oligomerization is effected in the liquid phase and the ethene is fully dissolved in the olefins having six carbon atoms. The olefins having six carbon atoms used as a reactive solvent are preferably diverted immediately before the etherification and recycled into the ethene oligomerization. This assumes that the process forms sufficient hexene; only a part of the $C_6$ fraction may be used as solvent since otherwise insufficient $C_6$ remains available for the etherification.

It will be appreciated that if a low $C_6$ formation rate does not allow the amount of hexene required as solvent to be recycled, $C_4$ olefin can also be used as a second solvent. This process variant is characterized in that the feedstock mixture comprises not only ethene but also olefins having four carbon atoms and olefins having six carbon atoms, wherein the reaction conditions of the first oligomerization and the composition of the feedstock mixture are chosen such that the first oligomerization is effected in the liquid phase and the ethene is fully dissolved in the olefins having four and six carbon atoms.

Finally it is also possible to use a solvent mixture which is partly inert and partly reactive. Thus for example a mixture of $C_6$ olefin and n-hexane and/or of n-butene and isobutene could be used as solvent. The above then applies correspondingly.

Preferably the first and/or the second oligomerization and preferably also the reaction of the second intermediate with the ethene are performed in the presence of the same heterogeneous catalyst. A solid body which is capable of catalysing all three reactions comprises at least two components, wherein the first component comprises at least one element selected from Ni, Cr, Fe, Ti which is present in metallic and/or oxidic and/or hydridic form and wherein the second component comprises at least one metal oxide selected from $Al_2O_3$, $SiO_2$, $TiO_2$, $ZrO_2$. An example of a catalyst of this kind is known from U.S. Pat. No. 2,581,228.

Typical reaction conditions for the first and second oligomerization over this catalyst in the liquid phase are in the following range:

Temperature: 20° C. to 150° C.
Pressure: $1*10^5$ Pa to $50*10^5$ Pa
Space/time loading: $3\ h^{-1}$ to $50^{-1}$ The reaction of the second intermediate with ethene in the presence of said catalyst is effected at a temperature between 20° C. and 150° C. and at a pressure between $1*10^5$ Pa and $50*10^5$ Pa, wherein the quantitative ratio of the ethene to the second intermediate is chosen such that the second intermediate is present in the liquid phase and the ethene is fully dissolved therein. This is achieved at a ratio of ethene to intermediate in the range from 0.1 to 0.5.

The etherification is effected in the liquid phase at a pressure of $1*10^5$ Pa to $7*10^5$ Pa and a temperature of 50° C. to 130° C. in the presence of a polystyrene-divinylbenzene copolymer bearing sulphonic acid groups or carboxylic acid groups. Said substance is for example an acidic ion exchange resin, for example Amberlyst® 15 from Rohm & Haas.

In the simplest case the alcohol used is methanol. The reaction of hexene with methanol to afford MTHxE is described in detail in:

Krause, A. O. I.; Hammarstrom, L. G.; Joutsimo, M.: Etherification of C6-Olefins with
Methanol. In Proceedings of the 8th International Congress on Catalysis, Berlin,
Germany, Jul. 2-6, 1984; Vol. V, V553-V563.

In contrast with the other reactions the cleavage reaction is preferably performed in the gas phase at a pressure of $1*10^5$ Pa to $25*10^5$ Pa and a temperature of 130° C. to 350° C. The ether cleavage can be heterogeneously catalysed with a solid body having the following composition which sums to 100 wt %:

silicon dioxide: 61 wt % to 74 wt %;
aluminum oxide: 19 wt % to 23 wt %;

magnesium oxide: 10 wt % to 12 wt %;
sum of other substances: 0 to 10 wt %.

The production of such a cleavage catalyst is described in EP1894621B1.

In the first oligomerization not only 1-hexene but in most cases also 2-hexene and 3-hexene are formed. Provided that it does not undergo further reaction it then ends up in the first reaction mixture. The yield of 1-hexene in the overall process can be enhanced when the 2-hexene and 3-hexene present in the first reaction mixture are separated by distillation from the 1-hexene and then subjected to an isomerization which isomerizes the 2-hexene and the 3-hexene to afford 1-hexene. The thus obtained isomerizate is recycled back into the removal of the 1-hexene from the 2-hexene and 3-hexene. The yield of 1-hexene is enhanced by separation of 2-hexene and 3-hexene and isomerization thereof.

The isomerization is effected in the gas phase at a temperature between 100° C. and 300° C. and at a pressure between $1*10^5$ Pa and $10*10^5$ Pa. The isomerization is heterogeneously catalysed over a solid catalyst which comprises as the catalytically active material at least one of the following oxides: MgO, CaO, BaO, $Li_2O$, SrO.

Specifically, basic catalysts may also be used in the isomerization. Such basic catalysts comprise as primary components aluminium oxide and/or zirconium oxide and/or abovementioned alkali metal oxides and/or alkaline earth metal oxides. Further components that may be present in the catalyst in amounts of 0.01 wt % to 3 wt %, preferably 0.5 wt % to 5 wt %, are titanium dioxide, silicon dioxide and/or thorium oxide. Such materials are disclosed in WO2004/052809A1.

Figure 1:
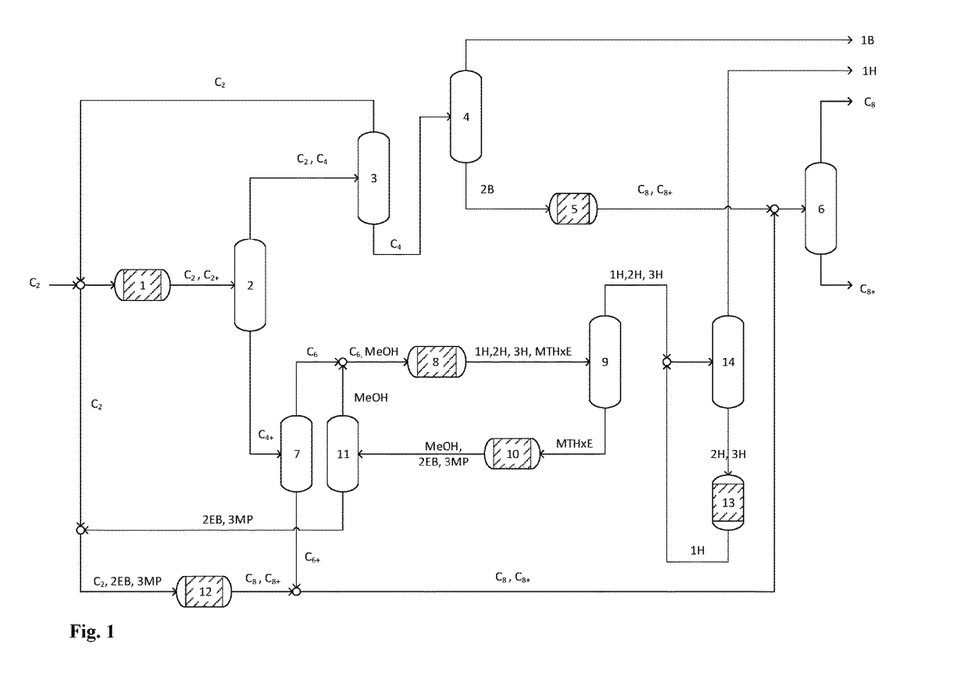
FIG. 1 representatively shows a basic implementation of the process for ethene feedstock.
Figure 2:
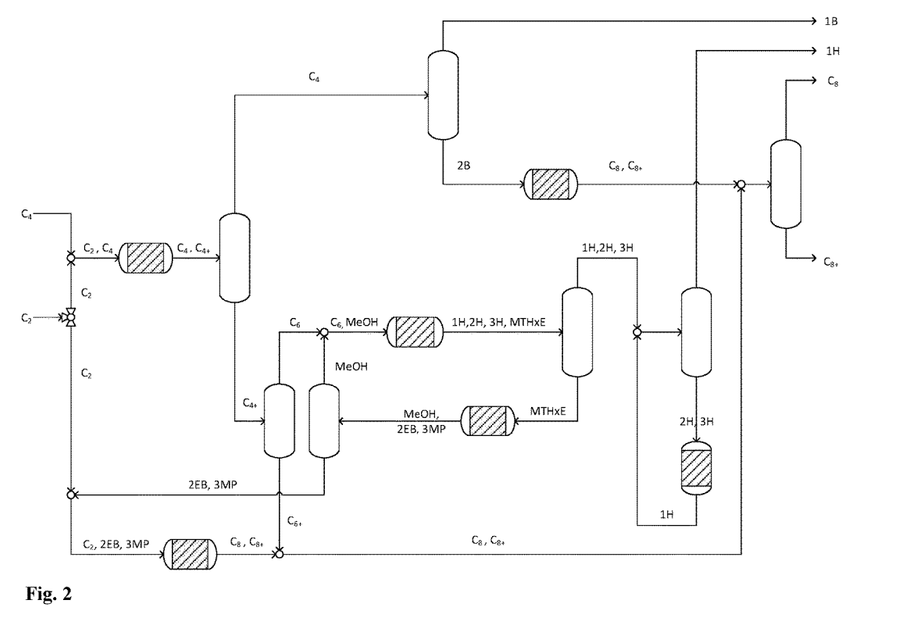
FIG. 2 representatively shows a basic implementation of the process for ethene and butene feedstock.
Figure 3:
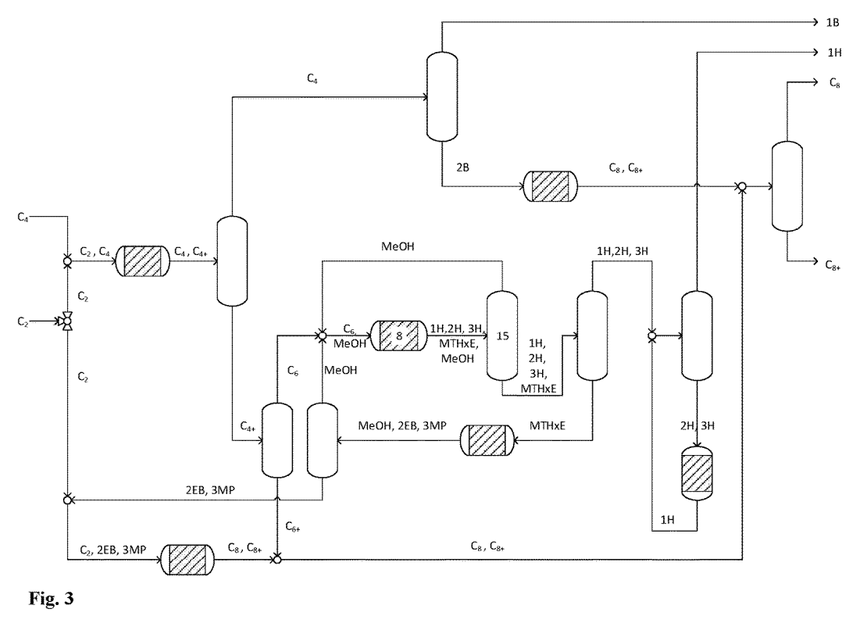
FIG. 3 representatively shows a basic implementation of the process for ethene and butene feedstock and but further including recycling of excess methanol.
Figure 4:
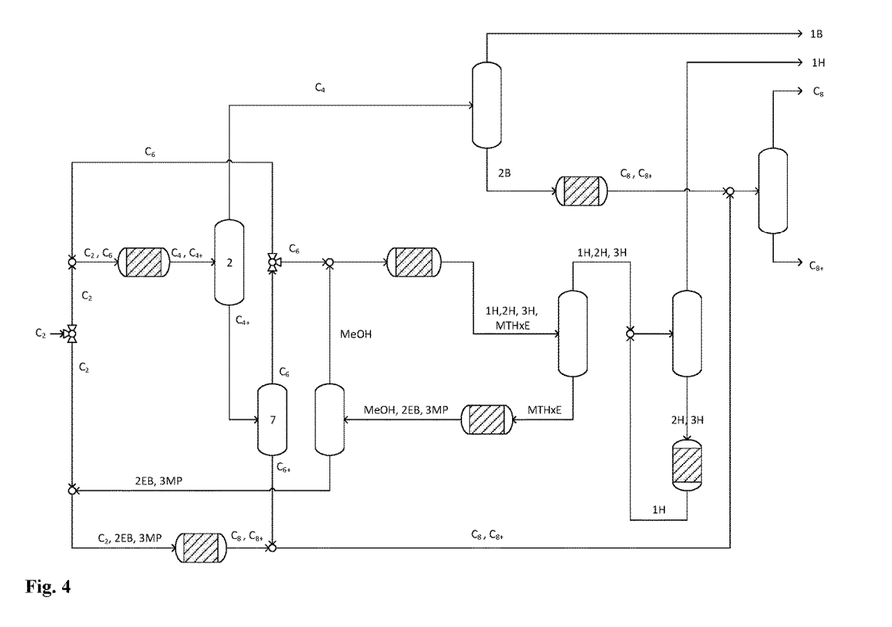
FIG. 4 representatively shows a basic implementation of the process with ethene feedstock using hexene as solvent.
Figure 5:
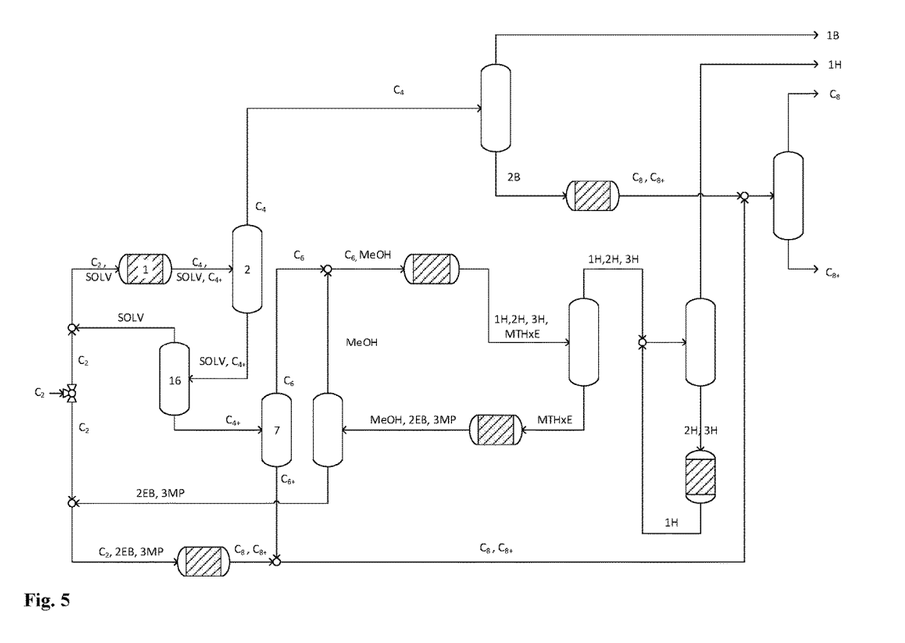
FIG. 5 representatively shows a basic implementation of the process with ethene feedstock using high-boiling solvent.
Figure 6:
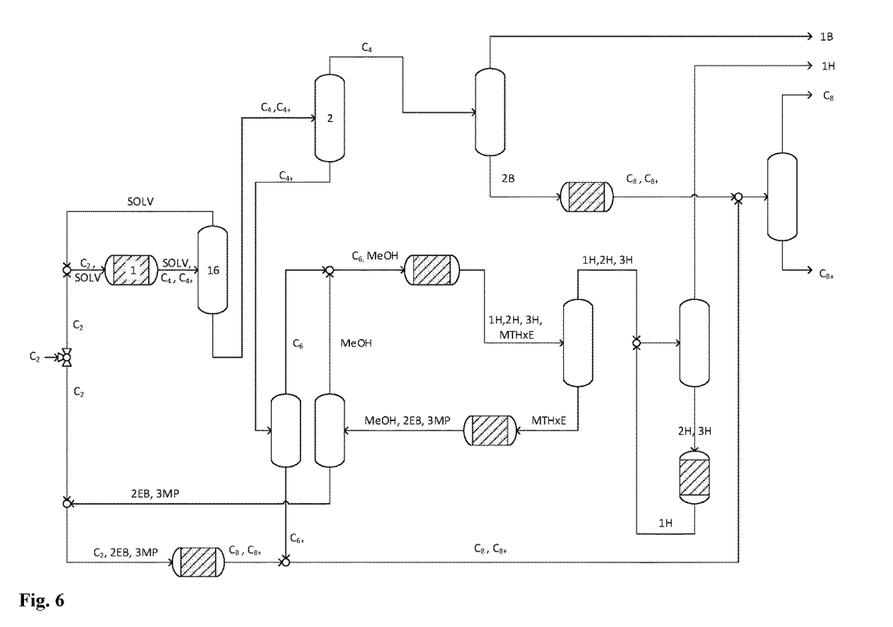
FIG. 6 representatively shows a basic implementation of the process with ethene feedstock using low-boiling solvent.

Various process variants are now to be elucidated with reference to simplified flow diagrams. The figures show the following:

FIG. 1: basic implementation, only ethene feedstock;
FIG. 2: implementation with ethene and butene feedstock;
FIG. 3: as FIG. 2 but further including recycling of excess methanol;
FIG. 4: implementation with only ethene feedstock using hexene as solvent;
FIG. 5: implementation with only ethene feedstock using high-boiling solvent;
FIG. 6: implementation with only ethene feedstock using low-boiling solvent;

FIG. 1 shows the simplest embodiment of the process. Ethene $C_2$ is provided as feedstock. Purity >95%. In a first oligomerization 1 ethene is oligomerized in the gas phase over a heterogeneous catalyst.

The first oligomerization 1 is effected in the presence of a solid body which comprises at least two components, wherein the first component comprises at least one element selected from Ni, Cr, Fe, Ti which is present in metallic and/or oxidic and/or hydridic form and wherein the second component comprises at least one metal oxide selected from $Al_2O_3$, $SiO_2$, $TiO_2$, $ZrO_2$.

The first oligomerization 1 forms a first oligomerizate $C_2$, $C_{2+}$ comprising the oligomers $C_{2+}$ and unconverted ethene $C_2$. In a first distillation column a fraction $C_2$, $C_4$ comprising the unconverted ethene and the ethene dimers are removed overhead while the olefins having more than four carbon atoms $C_{4+}$ are withdrawn from the bottom of the first distillation column 2.

In a second distillation column 3 the unconverted ethene $C_2$ is withdrawn overhead, recycled and mixed with freshly provided feed mixture.

A $C_4$ fraction $C_4$ comprising 1-butene, cis-2-butene and trans-2-butene is withdrawn from the bottom of the second distillation column 3. Thermal separation thereof is readily possible and is effected in a third distillation column 4. Obtained at the top of the third distillation column 4 is a third target fraction 1B comprising the 1-butene.

The two 2-butenes remain in the bottom of the third distillation column 4 and are withdrawn there as second intermediate 2B. The second intermediate 2B is subjected to a second oligomerization 5 to generate a second oligomerizate $C_8$, $C_{8+}$. This comprises sought-after octenes $C_8$, for example di-n-butene, and olefins having more than eight carbon atoms $C_{8+}$.

The second oligomerization 5 is effected in the presence of the solid body which comprises at least two components, wherein the first component comprises at least one element selected from Ni, Cr, Fe, Ti which is present in metallic and/or oxidic and/or hydridic form and wherein the second component comprises at least one metal oxide selected from $Al_2O_3$, $SiO_2$, $TiO_2$, $ZrO_2$.

The octenes are obtained from the second oligomerizate $C_8$, $C_{8+}$ as a first target fraction $C_8$ using a fourth distillation column at the top thereof. In the bottom thereof are the olefins having more than eight carbon atoms $C_{8+}$ which are discharged from the process as high boilers.

Back to the second distillation column 3, at the bottom of which are the olefins having more than four carbon atoms $C_{4+}$ which were formed in the ethene oligomerization 1. This includes a $C_6$ fraction $C_6$ which comprises at least 1-hexene, 3-methyl-cis-2-pentene, 3-methyl-trans-2-pentene and also 2-hexene, 3-hexene and 2-ethyl-1-butene. The $C_6$ fraction $C_6$ is obtained at the top of a fifth distillation column 7 and then subjected to an etherification 8.

The etherification is effected with methanol MeOH over an acidic ion exchange resin. In the etherification 8, 2-ethyl-1-butene, 3-methyl-cis-2-pentene, 3-methyl-trans-2-pentene are selectively reacted with the methanol to afford 3-methyl-3-methoxypentane. This ether is also known as methyl tert-hexyl ether (MTHxE). The first reaction mixture 1H, 2H, 3H, MTHxE withdrawn from the etherification 8 comprises not only MTHxE but also unconverted 1-hexene 1H and also 2-hexene 2H and 3-hexene 3H. This is because these linear hexenes 1H, 2H, 3H are not etherified to afford MTHxE.

By contrast, the branched $C_6$ olefins 2-ethyl-1-butene 2EB and also 3-methyl-cis-2-pentene and 3-methyl-trans-2-pentene 3MP are bound in the ether and can be withdrawn from the bottom of a sixth distillation column 9 as high-boiling ether fraction MTHxE.

According to the invention the ether fraction MTHxE is then retrocleaved to afford a mixture comprising 3-methyl-cis-2-pentene, 3-methyl-trans-2-pentene, 2-ethyl-1-butene and methanol which is described here as cleavage product MeOH, 2EB, 3MP.

The cleavage reaction 10 of the MTHxE is the reverse reaction of the etherification 8 and is effected in the gas phase over a solid catalyst comprising silicon dioxide, aluminum oxide and magnesium oxide. Since the ether fraction MTHxE is withdrawn from the bottom of the sixth distillation column 9 in liquid form an evaporation (not shown here) is first required.

The cleavage product MeOH, 2EB, 3MP is then separated in a seventh distillation column 11 into the alcohol MeOH and into a first intermediate 2EB, 3MP comprising the branched $C_6$ olefins 2-ethyl-1-butene, 3-methyl-cis-2-pentene and 3-methyl-trans-2-pentene.

The alcohol MeOH is recycled into the etherification 8 and thus fully reused.

The first intermediate 2EB, 3MP is reacted with ethene $C_2$ in a separate reactor 12 according to the teaching of the invention. This forms a second reaction mixture $C_8$, $C_{8+}$ comprising olefins having at least eight carbon atoms. In this way the undesired branched $C_6$ olefins 2EB and 3MP are converted into sought-after octenes $C_8$.

The reaction in the reactor 12 is effected in the presence of the same catalyst that is also employed in the first oligomerization 1 and the second oligomerization 5.

Since the second reaction mixture $C_8$, $C_{8+}$ is similar in composition to the second oligomerizate $C_8$, $C_{8+}$ obtained from the second oligomerization 5 and the bottoms product $C_{6+}$ from the fifth distillation column 7 these three fractions are mixed and worked up together in the fourth distillation column 6.

To enhance the yield of 1-hexene the plant shown in FIG. 1 features an isomerization 13 capable of converting 2-hexene and 3-hexene into 1-hexene. This is achieved over a heterogeneous catalyst comprising at least one of the oxides MgO, CaO, BaO, $Li_2O$, SrO as catalytically active material.

The isomerization 13 is arranged in the bottoms circuit of an eighth distillation column 14, at the top of which the first target fraction 1H is withdrawn with the 1-hexene. The eighth distillation column 14 is fed with the tops fraction from the sixth distillation column 9 comprising the linear hexanes 1H, 2H, 3H and with the 1-hexene obtained from the isomerization 13. Since the isomerization 13 is effected in the gas phase the bottoms circuit of the eighth distillation column 14 requires an evaporator upstream of the isomerization 13 (not shown in the figure).

The embodiment of the process shown in FIG. 2 is characterized in that the feedstock mixture comprises not only ethene $C_2$ but also olefins having four carbon atoms $C_4$, in particular 1-butene, cis-2-butene and trans-2-butene. Before the first oligomerization 1, these feedstocks are mixed such that the ethene is fully dissolved in the butene. The first oligomerization 1 then takes place in the liquid phase. The reaction is controlled such that the ethene is fully converted so that no separate removal of unconverted ethene is required. In case of traces of unconverted ethylene these may be discharged via the offgas stream from distillation column 2. The $C_4$ fraction $C_4$ is thus directly obtained at the top of the first distillation column 2. The remaining process steps are identical to that in FIG. 1.

The embodiment shown in FIG. 3 differs from the process shown in FIG. 2 by a ninth distillation column 15. Said column is used to remove methanol MeOH unconverted in the etherification 8 from the first reaction mixture and recycle it into the etherification 8. This is necessary in particular when methanol is fed into the etherification in superstoichiometric amounts.

FIG. 4 shows an embodiment where a part of the $C_6$ fraction $C_6$ obtained at the top of the fifth distillation column 7 is diverted and together with the ethene $C_2$ is sent to the first oligomerization 1. The other part of the $C_6$ fraction is sent to the etherification 8. The recycled $C_6$ olefin mixture $C_6$ serves as solvent for the ethene $C_2$ so that the first oligomerization 1 may be performed in the liquid phase. The ethene is dissolved in the liquid C6 olefin. Since the C6 olefin is reactive in the oligomerization correspondingly more C8 is formed. As a result the yield of hexene 1H is reduced. The advantage of this process variant is that it requires solely ethene as the feedstock since the reactive solvent $C_6$ is formed internally in the process. By contrast, in the process shown in FIG. 3 the reactive solvent $C_4$ needs to be supplied from outside as a feedstock.

FIGS. 5 and 6 each show a process variant employing an inert solvent SOLV which is recirculated and therefore likewise need not be supplied from outside.

In FIG. 5 an inert solvent SOLV that is high-boiling compared to butenes, such as n-heptane or n-hexane, is used. Ethene $C_2$ is fully dissolved therein and the first oligomerization 1 is therefore effected in the liquid phase. Since the solvent SOLV exhibits inert behavior it is not converted and ends up in the first oligomerizate $C_4$, SOLV, $C_{4+}$. In the first distillation column 2 it ends up in the bottoms since it has a higher boiling point than the C4-olefins C4 which go overhead in the first column 2. In order to separate the solvent SOLV from the olefins having more than four carbon atoms $C_{4+}$ a tenth distillation column 16 is provided. Said column separates the solvent overhead so that it may be fully recovered and fresh ethene $C_2$ may be dissolved therein. The olefins having more than four carbon atoms $C_{4+}$ are withdrawn from the bottom of the tenth distillation column 16 and as in the other embodiments sent to the fifth distillation column 7.

In FIG. 6 an inert solvent SOLV that is low-boiling compared to butenes, such as propane or isobutane, is used. Ethene $C_2$ is fully dissolved therein and the first oligomerization 1 is therefore effected in the liquid phase. Since the solvent SOLV exhibits inert behavior it is not converted and ends up in the first oligomerizate $C_4$, SOLV, $C_4$, $C_{4+}$. Since it is lower-boiling than the $C_4$ olefins $C_4$ the tenth distillation column 16 is arranged directly downstream of the first oligomerization 1. Therein, the solvent SOLV is removed overhead and recycled. The bottoms from the tenth distillation column 16 are sent to the first distillation column 2 and worked up therein in the same way as in the other embodiments.

Finally, the arrangement of the first distillation column 1 and the tenth distillation column 16 is reversed in the embodiments in FIGS. 5 and 6 since the solvent boils at a temperature higher in one case (FIG. 5) and lower in the other case (FIG. 6) than the butenes.

LIST OF REFERENCE SYMBOLS 1 first oligomerization
2 first distillation column
3 second distillation column
4 third distillation column
5 second oligomerization
6 fourth distillation column
7 fifth distillation column
8 etherification
9 sixth distillation column
10 cleavage reaction
11 seventh distillation column
12 reactor
13 isomerization
14 eighth distillation column
15 ninth distillation column
16 tenth distillation column
$C_2$ ethene (feedstock mixture)
$C_{2+}$ olefins having more than two carbon atoms
$C_4$ $C_4$ fraction comprising olefins having four carbon atoms
$C_{4+}$ olefins having more than four carbon atoms
$C_2$, $C_{2+}$ first oligomerizate
$C_6$: $C_6$ fraction comprising olefins having six carbon atoms
$C_{6+}$ $C_{6+}$ fraction comprising olefins having more than six carbon atoms
$C_8$: octene (second target fraction)

$C_{8+}$ $C_{6+}$ fraction comprising olefins having more than six carbon atoms
$C_8$, $C_{8+}$ second oligomerizate, second reaction mixture
1B 1-butene (third target fraction)
2B second intermediate comprising cis-2-butene and trans-2-butene
1H 1-hexene (first target fraction)
2H 2-hexene
3H 3-hexene
MeOH: methanol
MTHxE: ether fraction comprising 3-methyl-3-methoxypentane
1H, 2H, 3H, MTHxE first reaction mixture
2EB 2-ethyl-1-butene
3MP 3-methyl-cis-2-pentene and 3-methyl-trans-2-pentene
MeOH, 2EB, 3MP cleavage product
2EB, 3MP first intermediate
SOLV solvent

The invention claimed is:

1. A process for producing at least 1-hexene and octene from ethene comprising the steps of:
    a) providing a feedstock mixture comprising ethene;
    b) subjecting the ethene to a first oligomerization to obtain a first oligomerizate comprising olefins having less than six carbon atoms, $C_6$ olefins including 1-hexene, 3-methyl-cis-2-pentene, and 3-methyl-trans-2-pentene and olefins having more than six carbon atoms;
    c) distilling the first oligomerizate to obtain a $C_6$ fraction comprising 1-hexene, 3-methyl-cis-2-pentene, and 3-methyl-trans-2-pentene;
    d) subjecting the $C_6$ fraction to an etherification by addition of an alcohol in the presence of a heterogeneous catalyst to obtain a first reaction mixture comprising at least 1-hexene and 3-methyl-3-methoxypentane;
    e) distilling the first reaction mixture to obtain a first target fraction comprising 1-hexene and an ether fraction comprising at least 3-methyl-3-methoxypentane;
    wherein the improvement comprises:
    f) subjecting the ether fraction to a cleavage reaction to obtain a cleavage product which comprises 3-methyl-cis-2-pentene, 3-methyl-trans-2-pentene and the alcohol;
    g) removing the alcohol from the cleavage product by distillation and reusing said removed alcohol in the etherification;
    h) removing a first intermediate comprising at least 3-methyl-cis-2-pentene and 3-methyl-trans-2-pentene from the cleavage product by distillation;
    i) reacting the first intermediate with ethene to obtain a second reaction mixture comprising olefins having at least eight carbon atoms; and
    k) obtaining a second target fraction comprising octene from the second reaction mixture by distillation.

2. The process according to claim 1, wherein
the first oligomerizate further comprises 1-butene, cis-2-butene and trans-2-butene and 1-butene is recovered as follows:
    a) distilling the first oligomerizate to provide a $C_4$ fraction which comprises 1-butene, cis-2-butene and trans-2-butene;
    b) separating the $C_4$ fraction by distillation into a third target fraction comprising 1-butene and into a second intermediate which comprises cis-2-butene and trans-2-butene;
    c) subjecting the second intermediate to a second oligomerization to obtain a second oligomerizate which comprises olefins having at least eight carbon atoms;
    d) distilling the second oligomerizate together with the second reaction mixture to obtain the second target fraction.

3. The process according to claim 1, wherein the distillative workup of the first oligomerizate provides a $C_{6+}$ fraction which comprises olefins having more than six carbon atoms and in that the $C_{6+}$ fraction is worked up by distillation together with the second reaction mixture to obtain the second target fraction.

4. The process according to claim 2, wherein the distillative workup of the first oligomerizate provides a $C_{6+}$ fraction which comprises olefins having more than six carbon atoms and in that the $C_{6+}$ fraction is worked up by distillation together with the second reaction mixture and with the second oligomerizate to obtain the second target fraction.

5. The process according to claim 1, wherein the feedstock mixture comprises more than 95 wt % of ethene and that the reaction conditions of the first oligomerization are chosen such that the first oligomerization is affected in the gas phase in the presence of a heterogeneous catalyst.

6. The process according to claim 1, wherein the feedstock mixture comprises less than 25 wt % of ethene, in that the feedstock mixture comprises more than 75 wt % of a solvent, wherein the reaction conditions of the first oligomerization and the concentration of the ethene in the solvent are chosen such that the first oligomerization is affected in the liquid phase and the ethene is fully dissolved in the liquid solvent.

7. The process according to claim 5, wherein ethene unconverted in the first oligomerization is removed by distillation from the first oligomerizate and recycled into the first oligomerization.

8. The process according to claim 1, wherein the feedstock mixture comprises not only ethene but also olefins having four carbon atoms, wherein the reaction conditions of the first oligomerization and the composition of the feedstock mixture are chosen such that the first oligomerization is affected in the liquid phase and the ethene is fully dissolved in the olefins having four carbon atoms.

9. The process according to claim 1, wherein the feedstock mixture comprises not only ethene but also olefins having six carbon atoms, wherein the reaction conditions of the first oligomerization and the composition of the feedstock mixture are chosen such that the first oligomerization is affected in the liquid phase and the ethene is fully dissolved in the olefins having six carbon atoms.

10. The process according to claim 1, wherein the feedstock mixture comprises not only ethene but also olefins having four carbon atoms and olefins having six carbon atoms, wherein the reaction conditions of the first oligomerization and the composition of the feedstock mixture are chosen such that the first oligomerization is affected in the liquid phase and the ethene is fully dissolved in the olefins having four and six carbon atoms.

11. The process according to claim 1, wherein a solid body comprising at least two components is employed as a heterogeneous catalyst in one or more of the following reactions:
    in the first oligomerization;
    in the second oligomerization;
    in the reaction of the second intermediate with ethene;
    wherein the first component comprises at least one element selected from Ni, Cr, Fe, Ti which is present in metallic and/or oxidic and/or hydridic form and wherein the second component comprises at least one metal oxide selected from $Al_2O_3$, $SiO_2$, $TiO_2$, $ZrO_2$.

12. The process according to claim 11, wherein the reaction of the second intermediate with ethene is effected in the presence of said catalyst, wherein this reaction is affected at a temperature between 20° C. and 150° C. and at a pressure between $1*10^5$ Pa and $50*10^5$ Pa, wherein the quantitative ratio of the ethene to the second intermediate is chosen such that the second intermediate is present in the liquid phase and the ethene is fully dissolved therein.

13. The process according to claim 1, wherein the cleavage reaction is effected in the gas phase at a pressure of $1*10^5$ Pa to $25*10^5$ Pa and a temperature of 130° C. to 350° C. in the presence of a solid body having the following composition which sums to 100 wt %:
    silicon dioxide: 61 wt % to 74 wt %;
    aluminum oxide: 19 wt % to 23 wt %;
    magnesium oxide: 10 wt % to 12 wt %;
    sum of other substances: 0 to 10 wt %.

14. The process according to claim 1, wherein the etherification is affected in the liquid phase at a pressure of $1*10^5$ Pa to $7*10^5$ Pa and a temperature of 50° C. to 130° C. in the presence of a polystyrene-divinylbenzene copolymer bearing sulfonic acid groups or carboxylic acid groups.

15. The process according to claim 2, wherein the cleavage reaction is affected in the gas phase at a pressure of $1*10^5$ Pa to $25*10^5$ Pa and a temperature of 130° C. to 350° C. in the presence of a solid body having the following composition which sums to 100 wt %:
    silicon dioxide: 61 wt % to 74 wt %;
    aluminum oxide: 19 wt % to 23 wt %;
    magnesium oxide: 10 wt % to 12 wt %;
    sum of other substances: 0 to 10 wt %.

16. The process according to claim 2, wherein the etherification is affected in the liquid phase at a pressure of $1*10^5$ Pa to $7*10^5$ Pa and a temperature of 50° C. to 130° C. in the presence of a polystyrene-divinylbenzene copolymer bearing sulfonic acid groups or carboxylic acid groups.

17. The process according to claim 2, wherein a solid body comprising at least two components is employed as a heterogeneous catalyst in one or more of the following reactions:
    in the first oligomerization;
    in the second oligomerization;
    in the reaction of the second intermediate with ethene;
    wherein the first component comprises at least one element selected from Ni, Cr, Fe, Ti which is present in metallic and/or oxidic and/or hydridic form and wherein the second component comprises at least one metal oxide selected from $Al_2O_3$, $SiO_2$, $TiO_2$, $ZrO_2$.

18. The process according to claim 2, wherein the feedstock mixture comprises not only ethene but also olefins having six carbon atoms, wherein the reaction conditions of the first oligomerization and the composition of the feedstock mixture are chosen such that the first oligomerization is affected in the liquid phase and the ethene is fully dissolved in the olefins having six carbon atoms.

19. The process according to claim 2, wherein the feedstock mixture comprises not only ethene but also olefins having four carbon atoms and olefins having six carbon atoms, wherein the reaction conditions of the first oligomerization and the composition of the feedstock mixture are chosen such that the first oligomerization is affected in the liquid phase and the ethene is fully dissolved in the olefins having four and six carbon atoms.

20. The process according to claim 2, wherein the feedstock mixture comprises not only ethene but also olefins having four carbon atoms, wherein the reaction conditions of the first oligomerization and the composition of the feedstock mixture are chosen such that the first oligomerization is affected in the liquid phase and the ethene is fully dissolved in the olefins having four carbon atoms.

* * * * *